United States Patent
Hayashi

Patent Number: 5,452,881
Date of Patent: Sep. 26, 1995

[54] CRUCIBLE FOR AN ANALYZER

[75] Inventor: Morinobu Hayashi, Miyanohigashi, Japan

[73] Assignee: Horiba Ltd., Kyoto, Japan

[21] Appl. No.: 148,469

[22] Filed: Nov. 5, 1993

[30] Foreign Application Priority Data

Nov. 7, 1992 [JP] Japan .................. 4-083066 U

[51] Int. Cl.⁶ .................................................. B01L 3/04
[52] U.S. Cl. .................... 266/79; 266/245; 266/275; 422/102; 373/118; 373/122; 432/262; 432/263
[58] Field of Search ............... 422/102, 78, 80; 266/275, 242, 79; 373/118, 122; 432/262, 263

[56] References Cited

U.S. PATENT DOCUMENTS

| | | | |
|---|---|---|---|
| 199,823 | 1/1878 | Glorieux | 422/102 |
| 1,007,990 | 11/1911 | Tharaldsen | 373/122 |
| 1,324,156 | 12/1919 | Jacoviello | 373/118 |
| 2,943,130 | 6/1960 | Lindner | 373/118 |
| 3,580,686 | 5/1971 | Coulter | 356/246 |
| 3,627,432 | 12/1971 | Bergmann | 356/246 |
| 3,689,051 | 9/1972 | Miller | 266/39 |
| 3,923,464 | 12/1975 | Sitek et al. | 422/102 |
| 3,936,587 | 2/1976 | Sitek et al. | 13/23 |
| 4,056,677 | 11/1977 | Berk et al. | 13/23 |
| 4,149,754 | 12/1979 | Sitek et al. | 373/118 |
| 4,234,541 | 11/1980 | Bredweg et al. | 422/78 |
| 4,303,615 | 12/1981 | Jurmell et al. | 422/102 |
| 4,328,386 | 5/1982 | Bredweg et al. | 373/118 |
| 4,372,543 | 2/1983 | Gardiner | 266/275 |
| 4,422,625 | 12/1983 | Thurn | 266/281 |
| 4,708,738 | 11/1987 | Masterson et al. | 75/59.1 |
| 4,921,222 | 5/1990 | Mott | 266/275 |
| 5,236,353 | 8/1993 | Adani et al. | 432/198 |

FOREIGN PATENT DOCUMENTS

| | | |
|---|---|---|
| 0392066 | 4/1989 | European Pat. Off. . |
| 397764 | 6/1924 | Germany . |
| 237368A1 | 7/1986 | Germany . |
| 410876A1 | 3/1991 | Germany . |
| 1295664 | 3/1969 | United Kingdom . |
| 1497230 | 4/1975 | United Kingdom . |
| 0657227 | 4/1979 | United Kingdom . |
| 12268 | 4/1989 | United Kingdom . |
| 9015333 | 12/1990 | WIPO . |

Primary Examiner—Robert J. Warden
Assistant Examiner—N. Bhat
Attorney, Agent, or Firm—Price, Gess & Ubell

[57] ABSTRACT

An inexpensive crucible capable of obtaining a high analytical accuracy is provided. A circular projection is formed in a portion above a portion having an intermediate height on an inner circumferential surface of the graphite crucible to prevent contamination of the sample gases.

10 Claims, 2 Drawing Sheets

CRUCIBLE FOR AN ANALYZER

BACKGROUND OF THE INVENTION

1. Field of the Invention

The present invention relates to an improved crucible used in an analyzer for quantitatively analyzing elements contained in a sample such as metallic materials and ceramics.

2. Description of Related Art

In an analyzer for quantitatively analyzing elements contained in a sample such as metallic materials and ceramics, usually a graphite crucible is positioned between a set of electrodes which are arranged in a vertical manner within a sample-extracting furnace under airtight conditions. The sample is put in the graphite crucible, and a large electric current is passed between both electrodes while supplying an inert gas as a carrier gas to heat the graphite crucible. The sample is melted and generates a sample gas which is collected in an analyzer to enable an analysis of the elements in the sample.

Prior to such an analysis of the elements, the graphite crucible is heated to high temperatures prior to introducing the sample to conduct a degassing treatment, also called preheating, for removing impurities such as various gases including water.

However, in the above-described degassing treatment, while the graphite crucible is heated to high temperatures of about 3,000° C., an upper electrode made of copper alloys is strongly cooled with water, so that a temperature in the vicinity of the upper electrode is not as high. Thus, a sufficient degassing cannot be achieved. As a result, gaseous elements to be measured, such as CO, N, and H, may remain in an upper portion of the graphite crucible.

In such a case, when the sample is put in the graphite crucible to extract the sample gas, the molten sample rises to an upper portion of the graphite crucible to release any gaseous elements remaining in the graphite crucible. Therefore, a problem has occurred in that the gaseous elements are collected in the analyzer together with sample elements released from the sample itself. Thus, accurate analytical values are not obtained and reliability is lowered.

In order to solve such a problem, a so-called double crucible capable of indirectly heating the sample has been used. Such a system is disposable; therefore, another problem has occurred in that cost is increased.

OBJECTS AND SUMMARY OF THE INVENTION

It is an object of the present invention to provide an inexpensive crucible capable of obtaining high analytical accuracy.

A crucible such as graphite according to the present invention is characterized in that a circular projection on an inner circumferential surface is formed in a portion of the crucible above an intermediate height. The circular projection formed above the intermediate height of the graphite crucible prevents a molten sample from rising. Thus, even if any remaining gases exist in the vicinity of an upper electrode during a preheating, the remaining gases can be prevented from being outgassed with the elements of the molten sample. Thus, only sample components extracted from a sample itself will be introduced into an analyzer.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an improved graphite crucible.

Figure 1:
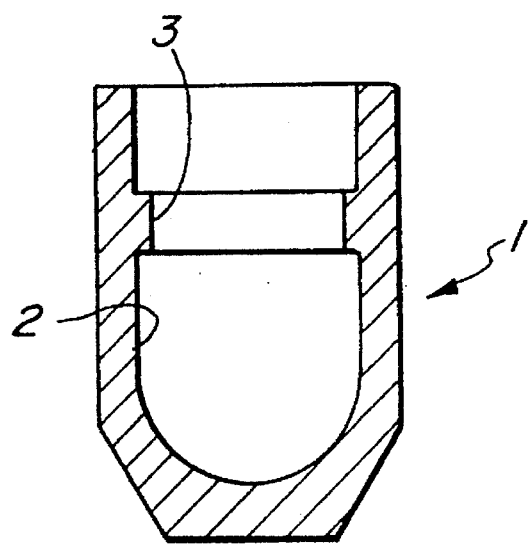
FIG. 1 is a longitudinal cross-sectional view showing one preferred embodiment of a graphite crucible according to the present invention.
Figure 2:
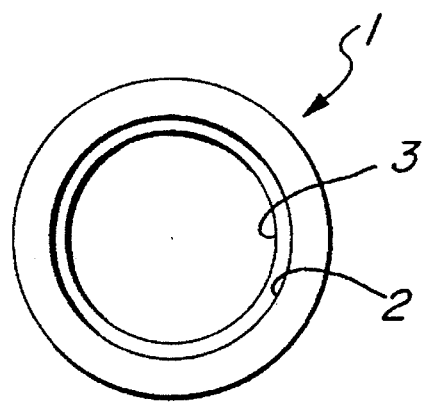
FIG. 2 is a top plan view of FIG. 1.

FIG. 1 is a longitudinal cross-sectional view showing a graphite crucible 1. FIG. 2 is a top plan view of the graphite crucible 1. The graphite crucible 1 is constructed in the form of a cylindrical container having a bottom surface and provided with a circular projection 3 formed in an upper portion of an inner circumferential surface 2 thereof. The crucible of the present invention could also be made of a ceramic such as BN and $TiB_2$. The crucible body has an upper open cavity wall and a radiallyreduced portion at an intermediate level. The circular projection, protrusion or flange 3 is of sufficient size to prevent a molten sample 4 from rising when a sample is extracted. For example, assuming a crucible body of 22 mm in height, an outer diameter of 14 mm, and an inner diameter of 11.5 mm, the projection 3 will be located at a position 2 mm from the upper edge and will project inward from the inner diameter by 1 mm with a thickness of 1 mm.

Thus, even if gaseous elements, such as CO, $N_2$, and $H_2$, remain in the upper portion of the graphite crucible 1 after a preheating, they can be prevented from being outgassed when the molten sample 4 is gasified. As a result, only the sample elements can be carried by a carrier gas to be extracted as sample gases and a high analytical accuracy can be achieved.

Figure 3:
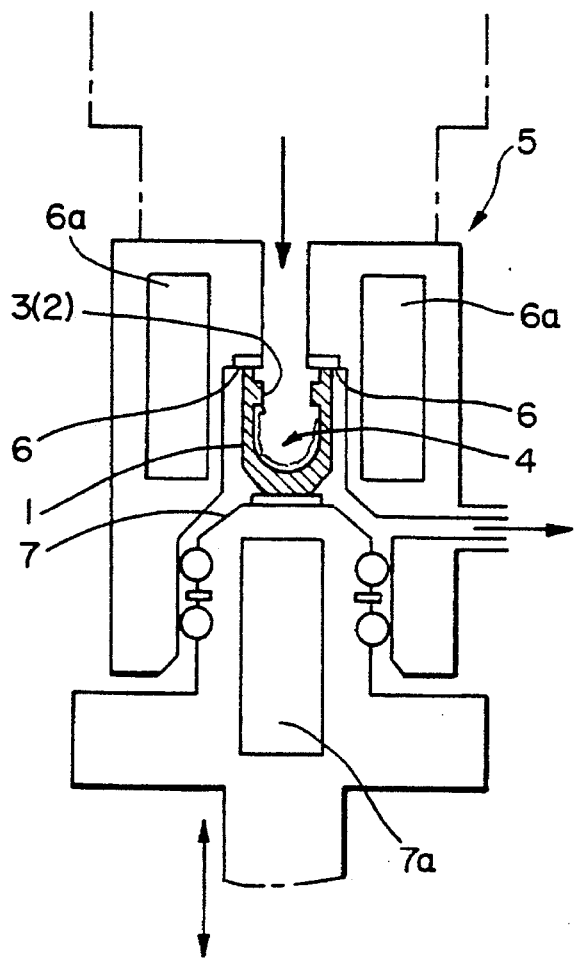
FIG. 3 is a partial cross-sectional view showing a sample-extracting furnace.

The graphite crucible 1 is set between upper electrodes 6, 6, which are fixedly arranged in an upper portion of a sample-extracting furnace 5, as shown in FIG. 3. A lower electrode 7 is movably mounted to travel in an up-and-down motion below the upper electrodes 6, 6. At first, a preheating operation is conducted for heating an empty graphite crucible 1 to a high temperature without putting the sample 4 in the graphite crucible 1. This operation will remove most of the impurities such as gases including water.

In the preheating, a large electric current is applied between both electrodes 6, 6 under the condition that the sample-extracting furnace 5 is maintained airtight and the graphite crucible 1 is heated to high temperatures of about 3,000° C. The upper electrodes 6 have slots (not shown) to permit the gases to be released.

However, the upper electrodes 6 are made of copper alloys, and it is thus necessary to strongly cool them with water. Consequently, a cooling water is passed through a water flow passage 6a formed within the upper electrodes 6. Accordingly, there is a tendency that a temperature of the upper electrode 6 itself is suppressed so as to be relatively lower than the ambient gases. Thus an upper portion, where the graphite crucible 1 is brought into contact with the upper electrodes 6, has a relatively low temperature. Hence, a sufficient degassing cannot be achieved. On the other hand, the lower electrode 7 is usually made of tungsten alloys with a greater heat resistance. As a result, a problem incidental to the upper electrodes 6 does not occur in spite of cooling with water by means of a water flow passage 7a.

After the above-described preheating, a sample 4 is put into the graphite crucible 1 from above the airtight sample-extracting furnace 5 to heat the sample 4 together with the graphite crucible 1 while supplying an outside inert gas as the carrier gas (see the arrow in FIG. 3), thereby melting the sample 4 and collecting the generated sample gases in an analyzer to analyze the elements.

In the above-described sample-extraction, a so-called rising phenomenon occurs in which the molten sample 4 rises along the inner circumferential surface 2 of the graphite crucible 1. This rising of the sample 4 can be prevented by the circular projection 3 formed in the upper portion of the inner circumferential surface 2 of the graphite crucible 1. Accordingly, even if gaseous elements which have not been outgassed by the preheating remain in the upper portion of the graphite crucible 1 as abovedescribed, they are not combined with the molten sample 4. Thus, a highly accurate analytical value can be obtained.

The circular projection 3 of the graphite crucible 1 has a lateral projection-like sectional shape in order to improve a rising-prevent effect. Alternatively, two or three circular projections (not shown) may be provided. These circular projections can be inexpensively formed in a relatively easy manner by machining a crucible blank.

Figure 4:
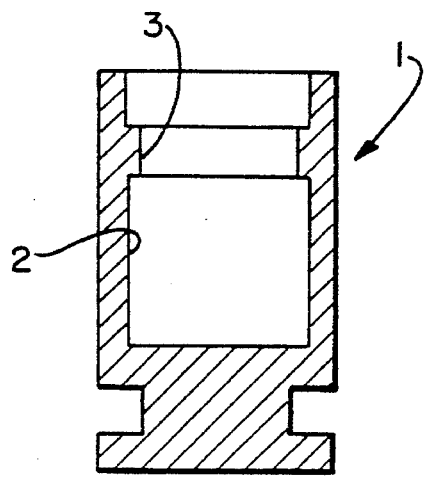
FIG. 4 is a longitudinal cross-sectional view showing another preferred embodiment.

FIG. 4 shows another preferred embodiment in which a similar circular projection 3 is formed in an upper portion of an inner circumferential surface 2 of a graphite crucible 1 of which its bottom portion has a brim shape. The undercuts or annular recesses in the base are located below the cavity bottom surface and prevent the crucible from being supercooled by the lower electrode 7.

The dimensions of the embodiment in FIG. 4 are a crucible body of 32 mm in height, an outer diameter of 14 mm, and an inner diameter of 11.6 mm. The projection 3 is located 2 mm from the upper open edge of the crucible body and is 1 mm in width and 1 mm in thickness.

As above-described, the graphite crucible 1 according to the present invention has the circular projection formed above the intermediate height of the inner circumferential surface of the crucible. Thus, any rising of the molten sample during the sample-extraction process can be effectively prevented, and the mingling of any remaining gaseous elements that were not released by the preheating can be prevented. Thereby the accuracy of the analytical value is improved and a stabilized and highly reliable analytical measurement is conducted even during continuous measurements. In addition, advantages occur in that such a graphite crucible can be easily and inexpensively produced, and the running cost per one analysis can be reduced in comparison with that in the case where a double crucible is required.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved analyzer crucible for melting samples to determine elements in the sample, comprising:

an analyzer crucible body having an upper opening edge with an open cavity wall and a bottom surface for receiving the sample, a circular protrusion is integrally formed with the crucible body and extends radially inward from and around the entire cavity wall below and adjacent the opening edge and the dimensions of the circular protrusion are sufficient to prevent the rising of the sample, when melted, above the circular protrusion by an underside surface of the circular protrusion which extends approximately perpendicularly from the cavity wall.

2. The invention of claim 1 wherein the crucible is made of graphite.

3. The invention of claim 1 wherein the crucible is made of a ceramic.

4. The invention of claim 1 wherein the crucible body has a base portion and a lower annular outer recess adjacent the base portion, the sample-receiving bottom surface being above the outer recess.

5. The invention of claim 4 wherein the crucible body has a height of approximately 32 mm, an outer diameter of approximately 14 mm, and the protrusion extends radially approximately 1 mm from the cavity wall.

6. An improved analytical furnace for combusting a sample, comprising:

a housing;

an upper electrode operatively mounted within the housing;

a lower electrode operatively mounted within the housing, the upper and lower electrodes being mounted in a spaced position;

a passageway through the housing to permit the passage of a carrier gas;

an analyzer crucible body is mounted between the upper and lower electrodes to hold a sample for combustion, the crucible body having an upper open edge contacting the upper electrode and an integral open cylindrical cavity wall and a bottom surface for receiving the sample, a circular flange is integrally formed with the crucibly body and extends continuously and radially inward and around the cavity wall adjacent the upper open edge, wherein the dimensions of the circular flange are sufficient to prevent the rising of the sample, when melted, above the circular flange by an underside surface of the circular flange which extends approximately perpendicularly from the cavity wall, the bottom surface is positioned adjacent the lower electrode so that the lower electrode contacts the crucible and an electric current sufficient to combust the sample can be passed between the electrodes to heat the crucible.

7. The invention of claim 6 wherein the crucible is made of graphite.

8. The invention of claim 6 wherein the crucible is made of a ceramic.

9. The invention of claim 6 wherein the crucible body has a base portion and a lower annular outer recess adjacent the base portion, the sample-receiving bottom surface being above the outer recess.

10. The invention of claim 9 wherein the crucible body has a height of approximately 32 mm, an outer diameter of approximately 14 mm, and the flange extends radially approximately 1 mm from the cavity wall.

* * * * *